US010849751B2

(12) United States Patent
Madjarov et al.

(10) Patent No.: US 10,849,751 B2
(45) Date of Patent: *Dec. 1, 2020

(54) METHOD AND APPARATUS FOR THERAPY OF AORTIC VALVE

(71) Applicant: Jeko Metodiev Madjarov, Charlotte, NC (US)

(72) Inventors: Jeko Metodiev Madjarov, Charlotte, NC (US); Charles R. Bridges, Charlotte, NC (US); Liam P. Ryan, Washington, DC (US)

(73) Assignee: JCOR-1, INC., Charlotte, NC (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/107,637

(22) Filed: Aug. 21, 2018

(65) Prior Publication Data

US 2018/0353296 A1 Dec. 13, 2018

Related U.S. Application Data

(63) Continuation of application No. 15/104,697, filed as application No. PCT/US2014/070621 on Dec. 16, 2014, now Pat. No. 10,111,750.

(Continued)

(51) Int. Cl.
*A61F 2/24* (2006.01)

(52) U.S. Cl.
CPC .......... *A61F 2/2445* (2013.01); *A61F 2/2442* (2013.01); *A61F 2220/0075* (2013.01);
(Continued)

(58) Field of Classification Search
CPC .... A61F 2/2442; A61F 2/2445; A61F 2/2448; A61F 2/2409; A61F 2250/0006; A61F 2250/0007; A61F 2250/0008
See application file for complete search history.

(56) References Cited

U.S. PATENT DOCUMENTS

2006/0106279 A1 5/2006 Machold et al.
2006/0241748 A1 10/2006 Lee et al.
(Continued)

FOREIGN PATENT DOCUMENTS

ES 2310092 A1 12/2008
WO WO-2014144439 A1 * 9/2014 .......... A61F 2/2445

OTHER PUBLICATIONS

International Search Report and Written Opinion issued in corresponding International Application No. PCT/US2014/070621 dated Mar. 27, 2015.

*Primary Examiner* — Dinah Baria
(74) *Attorney, Agent, or Firm* — Alston & Bird LLP

(57) ABSTRACT

A device (100) for supporting a valve annulus is described that includes spaced apart support members (105) and a connecting member (110) extending between and connecting the support members. At least one adjustor (115) is also provided that is engaged with the connecting member and can be actuated to modify a length of the connecting member between two adjacent support members. In addition, each support member may include at least two channels extending through the support members at different heights with respect to an overall thickness of the respective support member. Each channel may receive a portion of the connecting member therethrough, and each support member may further include a passageway between the channels to allow selection of one of the channels. In this way, the device may be adjusted in at least two dimensions to support the valve leaflets and promote sufficient closure of the leaflets.

17 Claims, 11 Drawing Sheets

Related U.S. Application Data

(60) Provisional application No. 61/923,066, filed on Jan. 2, 2014, provisional application No. 61/916,467, filed on Dec. 16, 2013.

(52) U.S. Cl.
CPC . *A61F 2250/001* (2013.01); *A61F 2250/0007* (2013.01); *A61F 2250/0008* (2013.01); *A61F 2250/0018* (2013.01); *A61F 2250/0036* (2013.01)

(56) References Cited

U.S. PATENT DOCUMENTS

| | | | |
|---|---|---|---|
| 2008/0065203 A1 | 3/2008 | Khalapyan | |
| 2009/0248148 A1* | 10/2009 | Shaolian | A61F 2/2448 623/2.37 |

\* cited by examiner

METHOD AND APPARATUS FOR THERAPY OF AORTIC VALVE

CROSS REFERENCE TO RELATED APPLICATIONS

This application is a continuation of U.S. patent application Ser. No. 15/104,697, filed Jun. 15, 2016, which is a U.S. National Stage Application under 35 U.S.C. § 371 of International Application No. PCT/US2014/070621, filed Dec. 16, 2014, which claims priority under 35 U.S.C. § 119 to U.S. Provisional Patent Application No. 61/916,467, filed Dec. 16, 2013, and to U.S. Provisional Patent Application No. 61/923,066, filed Jan. 2, 2014, each of which is hereby incorporated by reference in its entirety.

FIELD OF THE INVENTION

The present invention relates generally to methods and apparatuses for supporting the annulus of a valve. More specifically, methods and apparatuses are described for supporting and promoting sufficient closure of the aortic valve.

BACKGROUND

The heart is an organ made up mostly of muscle tissue that is responsible for circulating oxygenated blood through an organism's blood vessels using regular, repeated contractions. To facilitate the flow of blood in one direction into the heart, through its various chambers, and out to the rest of the body, the mammalian heart has four valves: the tricuspid valve, the pulmonary valve, the mitral valve, and the aortic valve.

In some cases, one of the valves may not function properly, such as due to a congenital defect or disease. The aortic valve, for example, which is responsible for allowing oxygenated blood to flow from the left ventricle of the heart to the aorta, in some cases may not fully open (known as stenosis). As a result, the amount of blood flowing through the heart is decreased, which can lead to serious complications such as atrial fibrillation, blood clots, lung congestion, heart enlargement, and heart failure, among others. In other cases, the aortic valve may not fully close (known as regurgitation or leakage). In these cases, blood from the aorta may leak back into the left ventricle, which may lead to problems such as atrial fibrillation, blood clots, infections, and heart failure, among others.

Accordingly, there is a need for a method and apparatus for supporting and promoting proper function of a valve, such as the aortic valve, in a way that is safe, robust, and simple to administer.

BRIEF SUMMARY OF EXAMPLE EMBODIMENTS

Accordingly, embodiments of a system and method are described that can provide support for a valve, such as the aortic valve, tricuspid valve, pulmonary valve, or mitral valve, in a way that allows the native valve to function as well as possible given its condition. Embodiments of a device for supporting a valve annulus may comprise a plurality of spaced apart support members configured to be sutured to tissue surrounding a valve opening so as to support leaflets of the valve to promote sufficient closure of the leaflets. The device may further include a connecting member extending between and connecting the support members and at least one adjustor engaged with the connecting member and configured to modify a length of the connecting member between two adjacent support members. Each support member may comprise at least two channels extending through at least a portion of a length of the respective support member at different heights with respect to an overall thickness of the respective support member. Furthermore, each channel may be configured to receive a portion of the connecting member therethrough, and each support member may comprise a passageway between the at least two channels. Each passageway may be configured to allow selection of one of the channels for receipt of the connecting member such that the device is configured to be adjusted in at least two dimensions to support the valve leaflets and promote sufficient closure of the leaflets. The device may comprise at least three support members.

In some cases, the connecting member may comprise a plurality of connecting members. Each connecting member may correspond to a different support member, and the at least one adjustor may be configured to receive ends of two connecting members corresponding to two adjacent support members. Moreover, the at least one adjustor may comprise an actuation portion. Actuation of the actuation portion in a first direction may draw one of the two adjacent support members towards the adjustor, and actuation of the actuation portion in a second direction may draw the other of the two adjacent support members towards the adjustor. For example, the actuation portion may comprise two actuation portions, and each actuation portion may be configured to adjust a position of a respective one of the two adjacent support members with respect to the adjustor.

In other embodiments, the at least one adjustor may comprise an actuation portion. Actuation of the actuation portion in a first direction may draw the two adjacent support members towards the adjustor, and actuation of the actuation portion in a second direction may move the two adjacent support members away from the adjustor. The distance between adjacent support members may be independently adjustable.

The connecting member may comprise nitinol. In some cases, the passageway of each support member may have a first width that is less than a width of each respective channel and less than a corresponding width of the connecting member received by the respective support member, and each support member may be configured such that a force applied along the thickness of the support member serves to increase a width of the passageway from the first width to a second width so as to allow the respective connecting member to pass therethrough. Furthermore, the support member may be configured such that the width of the passageway returns to the first width after the force applied to the support member is removed. In some cases, each support member may comprise at least three channels.

Each support member may define a length, and at least two of the support members may have different lengths. Additionally or alternatively, the length of the support members may be adjustable.

In still other embodiments, a method of supporting a valve annulus is provided, where the method includes suturing each of a plurality of support members to tissue surrounding a valve opening so as to support leaflets of the valve, wherein a connecting member extends between and connects the support members. The method may further include adjusting a first dimension corresponding to a distance between adjacent support members via at least one adjustor engaged with the connecting member, and adjusting a second dimension corresponding to a height of at least one of the support members with respect to the connecting member. Each support member may comprises at least two channels extending through at least a portion of a length of the respective support member at different heights with respect to an overall thickness of the respective support member, and each channel may be configured to receive a portion of the connecting member therethrough. Each support member may comprise a passageway between the at least two channels, and each passageway may be configured to allow selection of one of the channels for receipt of the connecting member to support the valve leaflets and promote sufficient closure of the leaflets.

In some cases, adjusting the first dimension may include actuating an actuation portion of the at least one adjustor in a first direction to draw one of the two adjacent support members towards the adjustor, and adjusting the first dimension may comprise actuating an actuation portion of the at least one adjustor in a second direction to draw the other of the two adjacent support members towards the adjustor. Alternatively, adjusting the first dimension may comprise actuating an actuation portion of the at least one adjustor in a first direction to draw the two adjacent support members towards the adjustor and actuating the actuation portion in a second direction to move the two adjacent support members away from the adjustor.

In some embodiments, adjusting the second dimension may comprise applying a force along the thickness of the support member so as to increase a width of the passageway from a first width, that is less than a width of each respective channel and less than a corresponding width of the connecting member received by the respective support member, to a second width so as to allow the respective support member to pass therethrough. The support member may be configured such that the width of the passageway returns to the first width after the force applied to the support member is removed. Moreover, in some cases, the method may further include adjusting a length of at least one of the plurality of support members.

BRIEF DESCRIPTION OF THE DRAWINGS

Figure 1:
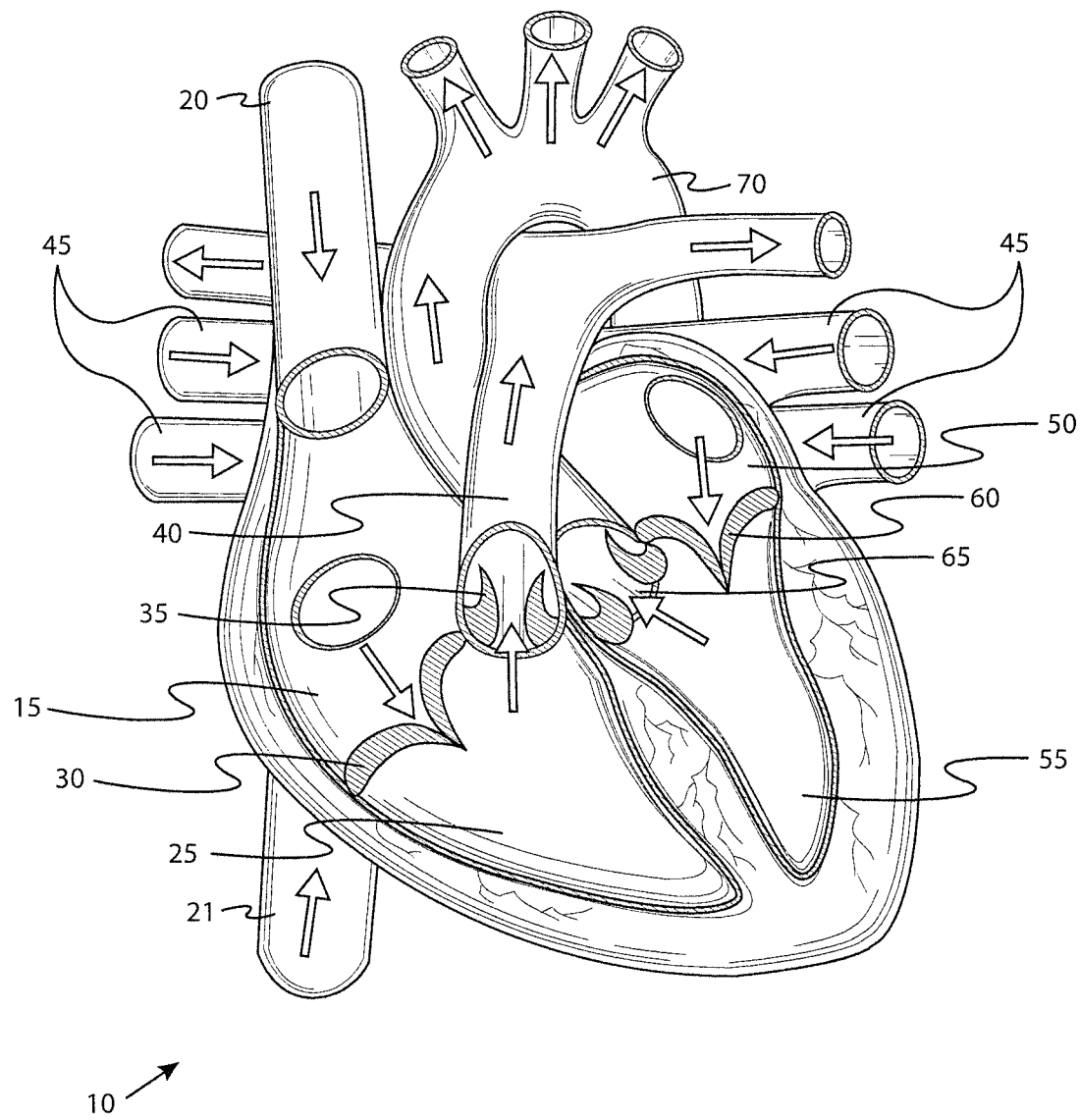
Figure 2:
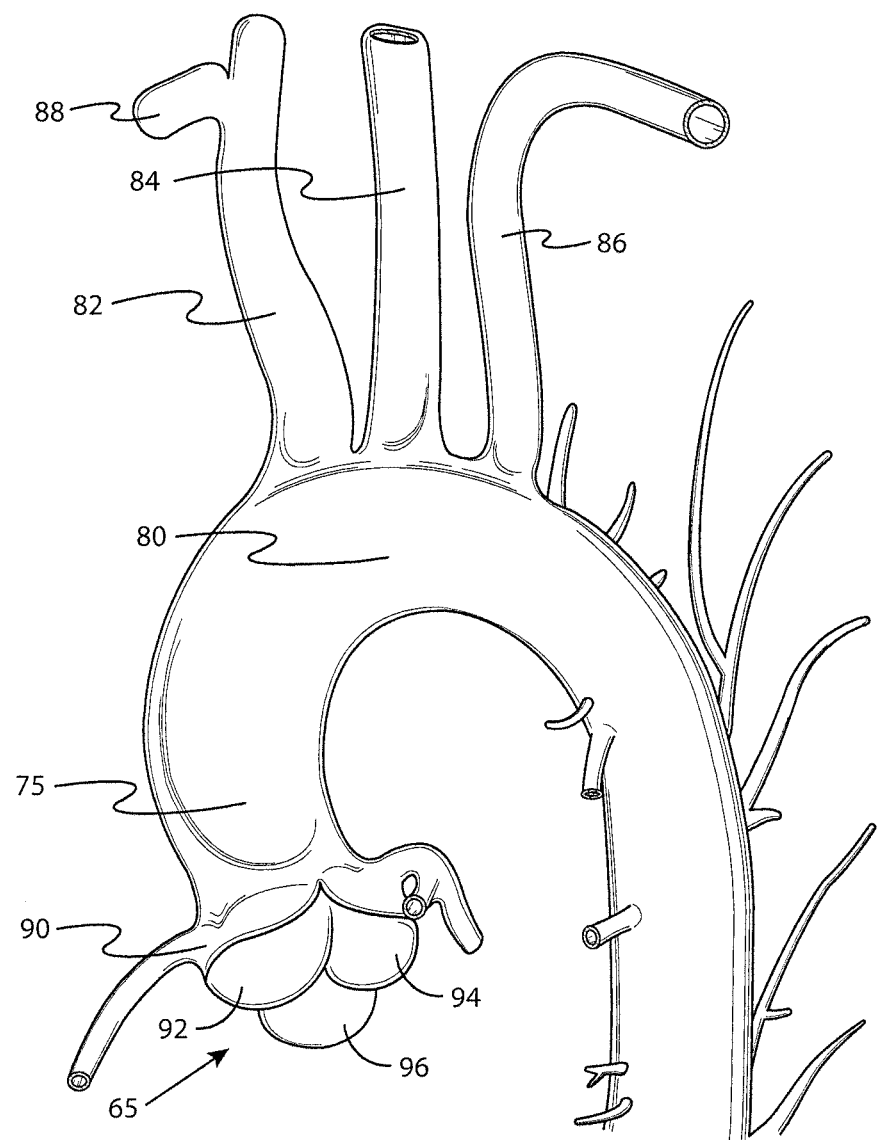
Figure 3:
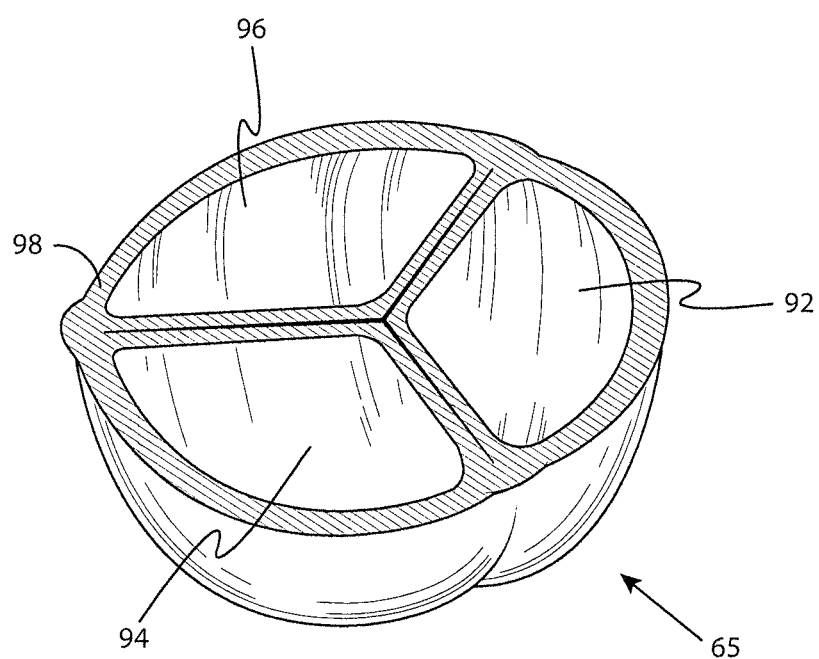
Figure 4:
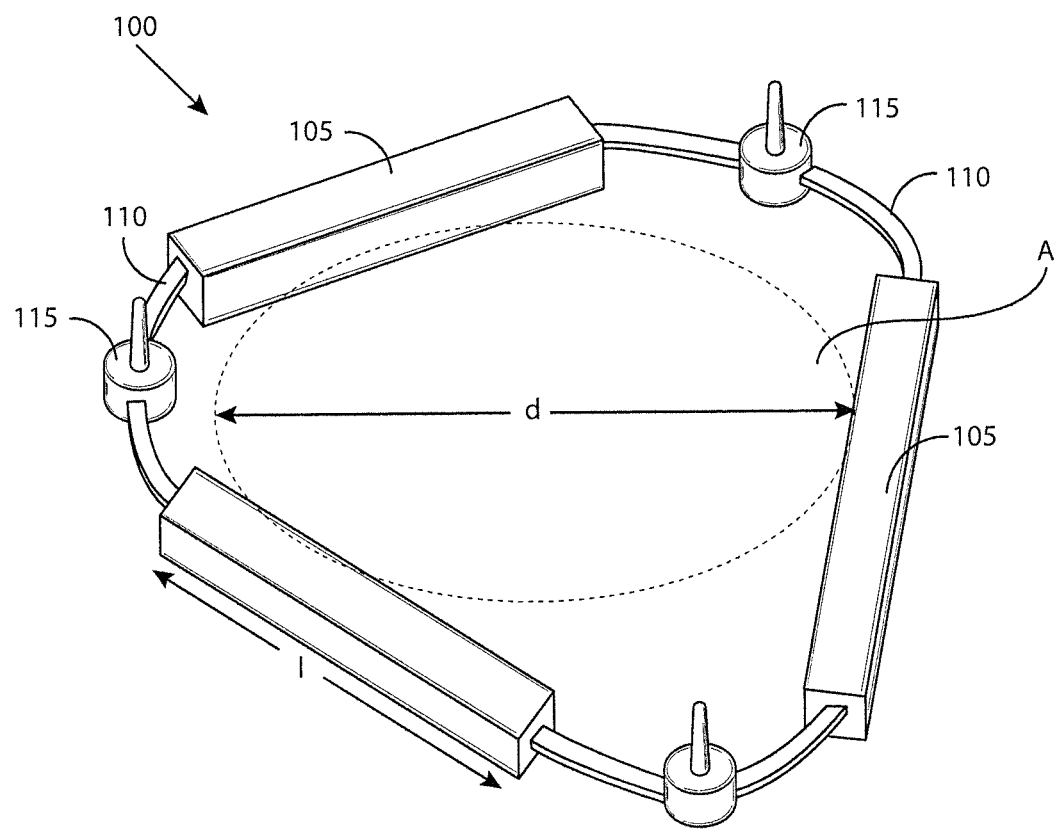
Figure 5:
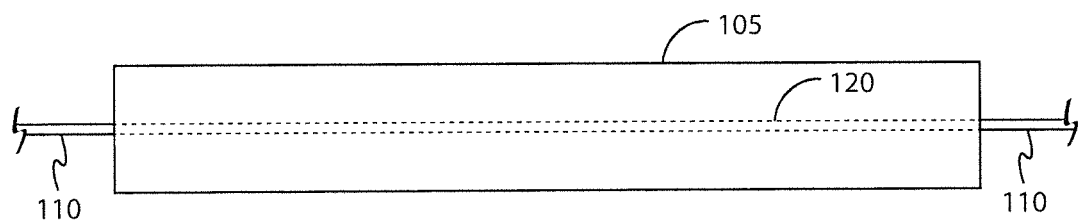
Figure 6:
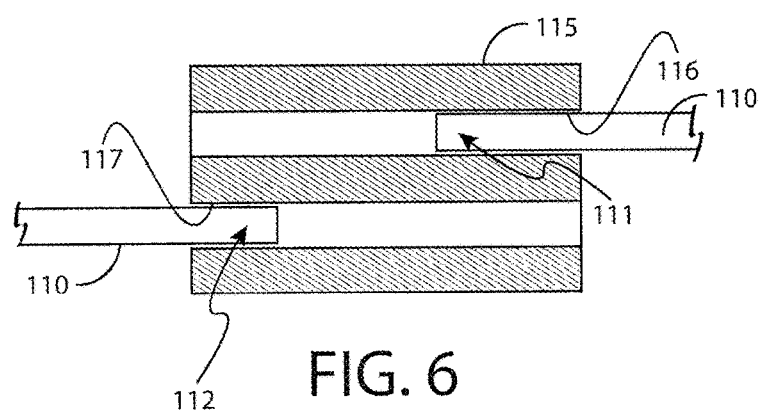
Figure 7:
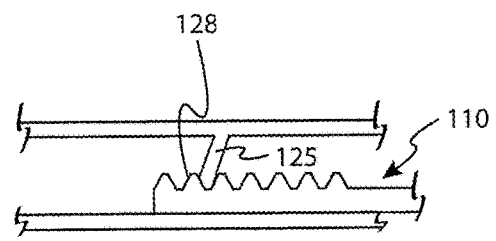
Figure 8A:
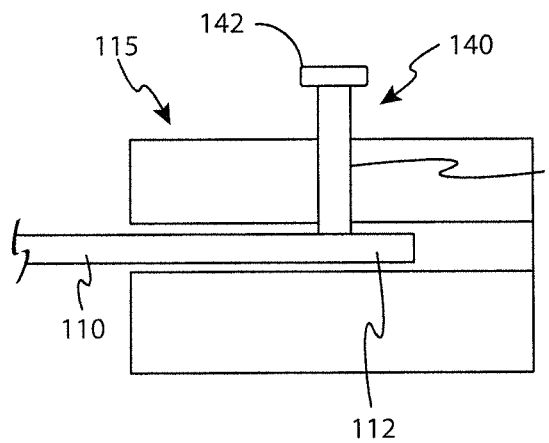
Figure 8B:
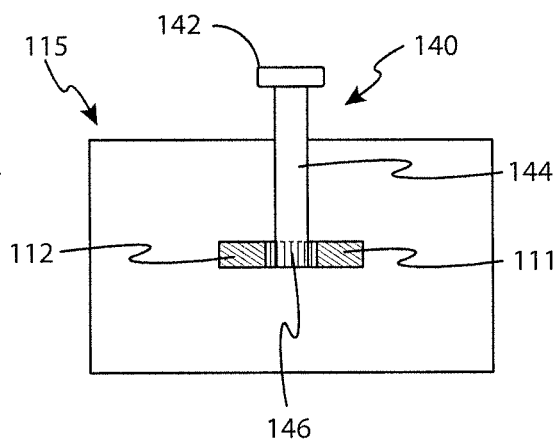
Figure 8C:
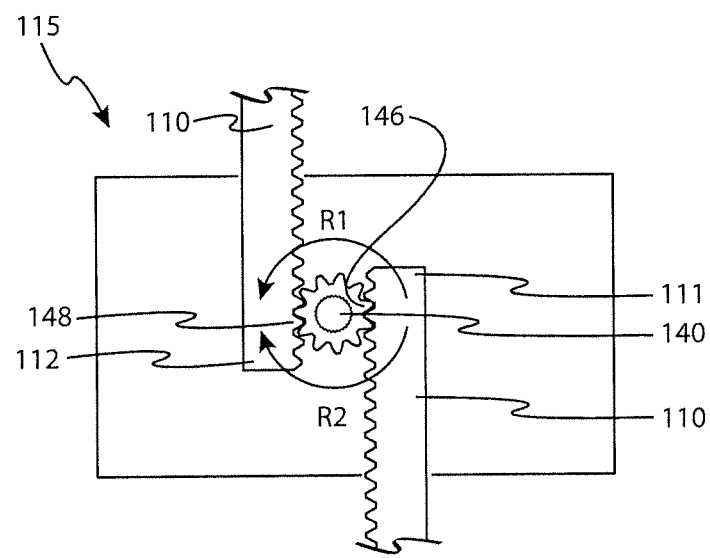
Figure 9:
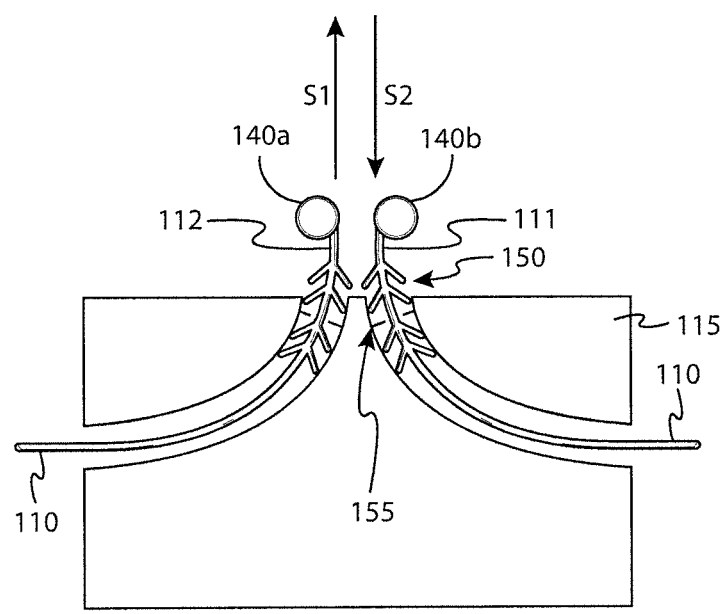
Figure 10:
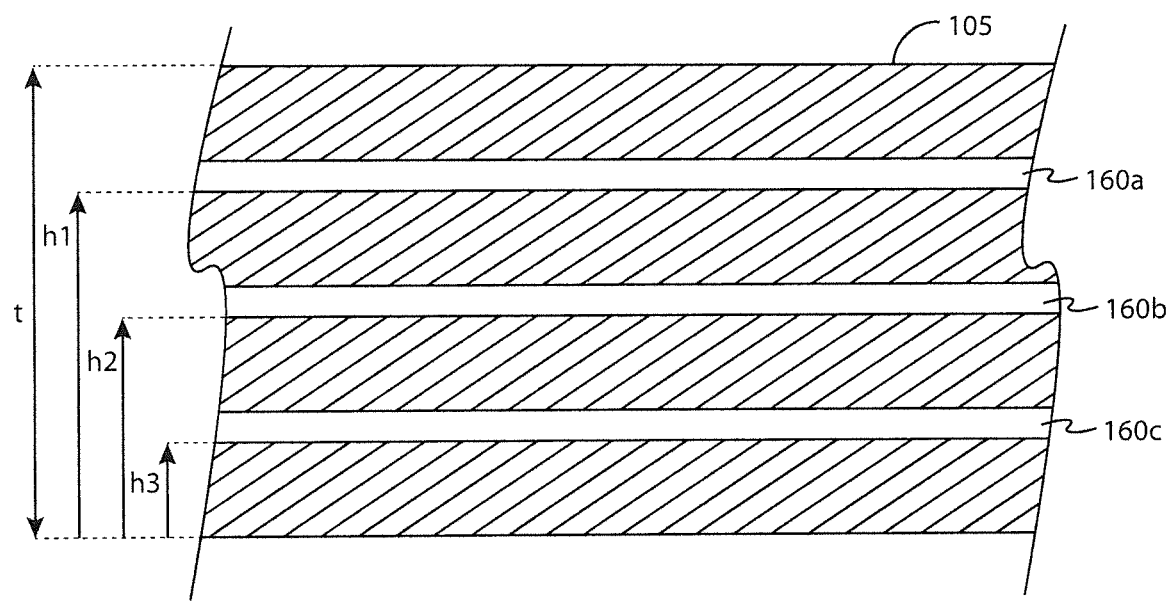
Figure 11A:
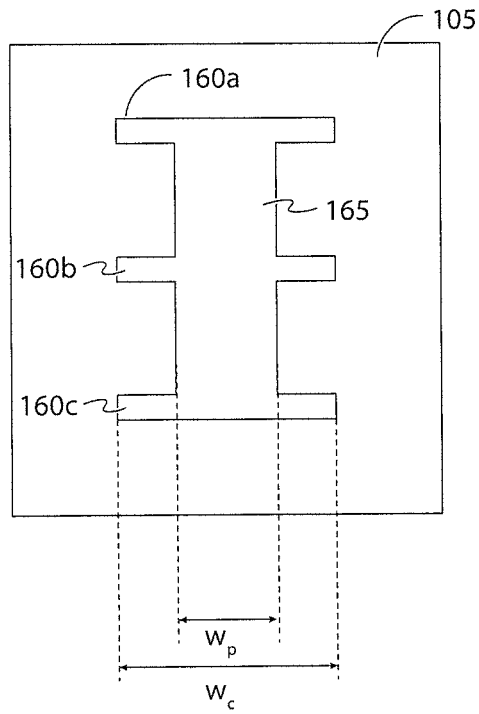
Figure 11B:
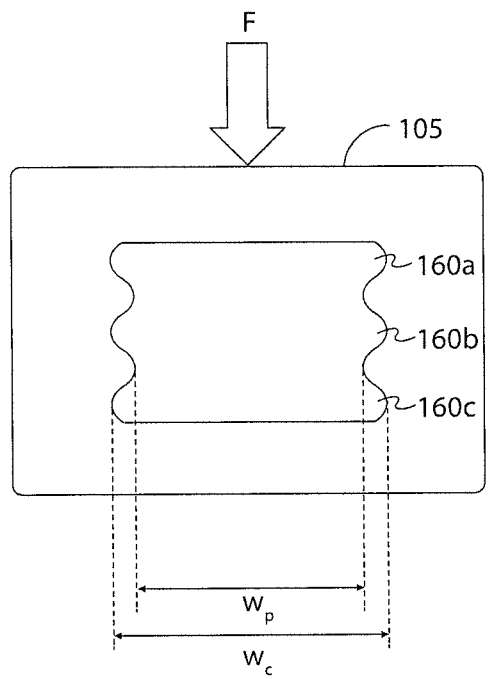
Figure 11C:
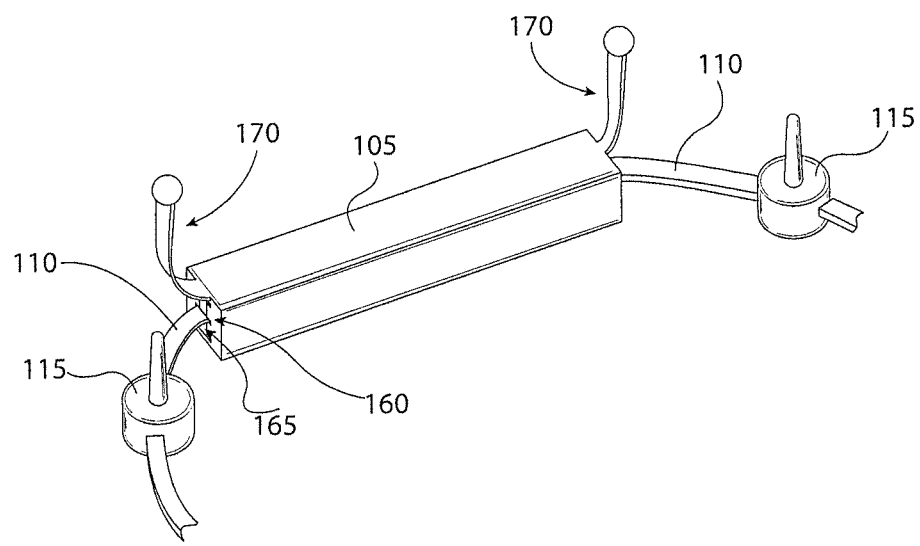
Figure 12:
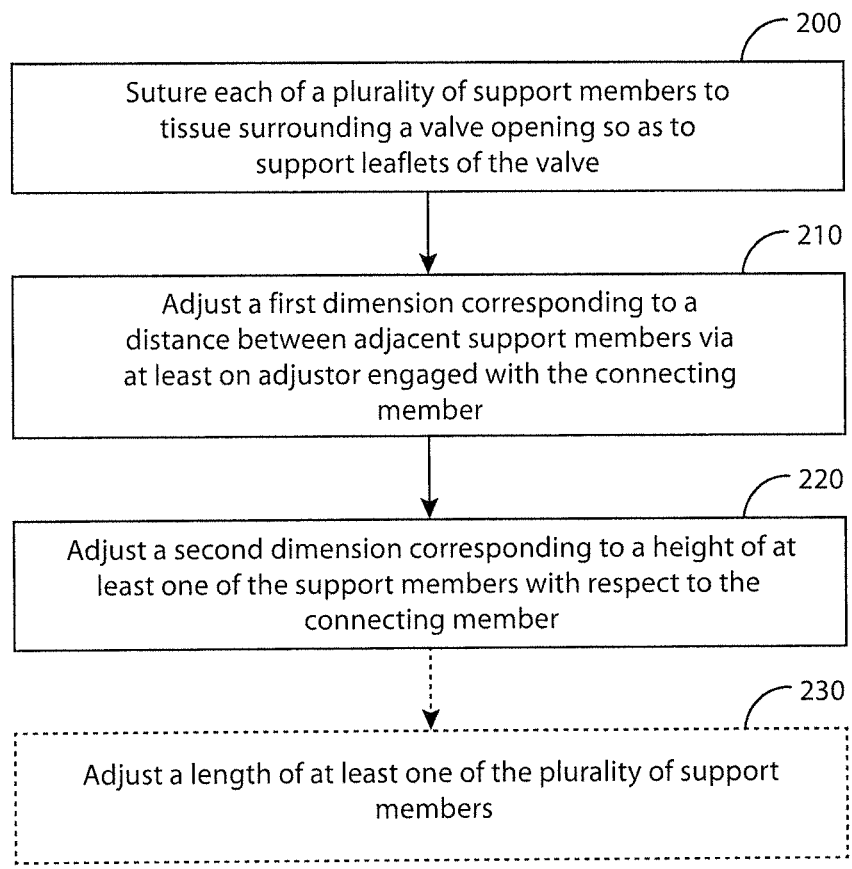

Having thus described the invention in general terms, reference will now be made to the accompanying drawings, which are not necessarily drawn to scale, and wherein:

FIG. 1 shows a schematic representation of a heart illustrating its various chambers and valves;

FIG. 2 shows a schematic representation of an aortic valve and aortic arch;

FIG. 3 shows schematic representation of an aortic valve;

FIG. 4 illustrates a perspective schematic representation of a device for supporting a valve annulus in accordance with an exemplary embodiment of the present invention;

FIG. 5 illustrates a plan view of a support member and connecting member of the device of FIG. 4 in accordance with an exemplary embodiment of the present invention;

FIG. 6 illustrates a cross sectional view of an adjustor in accordance with an exemplary embodiment of the present invention;

FIG. 7 illustrates a cross sectional view of an adjustor in accordance with another exemplary embodiment of the present invention;

FIG. 8A illustrates a side cross sectional view of an adjustor in accordance with another exemplary embodiment of the present invention;

FIG. 8B illustrates a front cross sectional view of the adjustor of FIG. 8A in accordance with an exemplary embodiment of the present invention;

FIG. 8C illustrates a top cross sectional view of the adjustor of FIG. 8A in accordance with an exemplary embodiment of the present invention;

FIG. 9 illustrates a cross sectional view of an adjustor in accordance with another exemplary embodiment of the present invention;

FIG. 10 illustrates a side cross sectional view of a support member in accordance with another exemplary embodiment of the present invention;

FIG. 11A illustrates a front cross sectional view of the support member of FIG. 10 before force is applied in accordance with an exemplary embodiment of the present invention;

FIG. 11B illustrates a front cross sectional view of the support member of FIG. 11A after force is applied in accordance with an exemplary embodiment of the present invention;

FIG. 11C illustrates a perspective view of the support member of FIG. 10 with handles in accordance with an exemplary embodiment of the present invention; and FIG. 12 illustrates a flowchart of a method of supporting a valve annulus using a device in accordance with an exemplary embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Although the examples described herein refer to aortic valve defects such as stenosis and regurgitation, embodiments of the described invention may be used to treat various aortic valve defects affecting the proper opening and/or closure of an aortic valve, both congenital and developed due to disease or other environmental factors. In addition, embodiments of the invention may also be used for the treatment of other valves, such as the mitral valve of the heart.

With reference to FIG. 1, the path of circulation of blood through the heart 10 will be described. In the human body, deoxygenated blood enters the right atrium 15 of the heart 10 via the superior vena cava 20 (from the upper half of the body) and the inferior vena cava 21 (from the lower half of the body). Once the right atrium 15 is full of blood, the pressure difference between the right atrium and the right ventricle 25 causes the tricuspid valve 30 to open, allowing blood to flow into the right ventricle 25. As the right ventricle 25 contracts, blood is pushed through the pulmonary valve 35 and into the lungs via the pulmonary artery 40, where the blood is re-oxygenated. Oxygenated blood from the lungs can then re-enter the heart 10 via the pulmonary veins 45 into the left atrium 50. The pressure differential between the left atrium 50 and the left ventricle 55 when the left atrium fills with blood then causes the mitral valve 60 to open, and blood is allowed to flow from the left atrium to the left ventricle. Finally, contraction of the left ventricle 55 forces the aortic valve 65 to open and pushes blood into the aorta 70, from which oxygenated blood is circulated through the vasculature.

The tricuspid valve 30, the pulmonary valve 35, and the aortic valve 65 are tricuspid valves in approximately 99% of the human population, meaning that there are three leaflets that cooperate to close the valve opening, whereas the mitral valve 60 is a bicuspid valve having two leaflets. Proper functioning of the valves 30, 35, 60, and 65 is essential to proper blood flow through the heart 10. In some cases, however, whether due to congenital defects or disease, one or more of the valves may not open or close as it should. For example, the aortic valve 65 may suffer from stenosis, or a narrowing of the valve that keeps the valve from fully opening to allow blood to flow into the aorta 70. In other cases, the aortic valve 65 may not fully close (referred to as leakage or regurgitation). Both conditions are undesirable and can cause serious consequences to the body, such as atrial fibrillation, blood clots, and heart failure, among others.

With reference to FIG. 2, the ascending aorta 75 is the portion of the aorta 70 that starts at the upper part of the base of the left ventricle and extends to the aortic arch 80, where the right common carotid artery 82, the left common carotid artery 84, and the left subclavian artery 86 (and in rare cases, the right subclavian artery 88) branch out to provide oxygenated blood to the upper thorax and the brain. The aortic root 90 is the part of the ascending aorta 75 that begins at the aortic annulus and extends to the sinotubular junction, where the aorta begins to have a tubular structure.

As noted above, and with reference to FIGS. 2 and 3, the aortic valve 65 is has three leaflets, or cusps—the left coronary cusp 92, the right coronary cusp 94, and the non-coronary cusp 96 (located posteriorly to the left and right coronary cusps). The aortic valve 65 and the root 90 of the aorta 70 are supported against the forces imparted by the beating heart by the aortic valve annulus 98 (shown in FIG. 3), which is part of the fibrous skeleton of the heart.

Conventional methods of treating aortic valve problems (e.g., stenosis and regurgitation) range from medication to surgery. If the damage done to the aortic valve and the surrounding heart tissue by the defect is not severe enough to require valve replacement, the existing aortic valve may be repaired using surgical techniques. Typically, open-heart surgery is required to perform aortic valve repairs. During this type of surgery, the patient is placed on a heart-lung machine, and the heart may be cooled to slow or stop the heartbeat. Depending on the particular type and extent of the defect, the surgeon may reshape the valve by removing excess valve tissue, add support to the aortic root 90 by adding tissue or other structure to the valve base, or attach the valve to nearby cord tissues.

For example, in cases in which the aortic valve 65 is a bicuspid valve (e.g., due to congenital defect) and does not need to be replaced, the aortic valve leaflets may be reshaped to allow the valve to open and close more completely. Although bicuspid aortic valve repair may be an option to treat leaking valves, such a procedure cannot be used to treat a stenotic or narrowed bicuspid aortic valve. As another example, if the valve leaflets have tears or holes, these defects can be patched by the surgeon with tissue patches.

In some cases, however, the aortic valve may be prolapsed, meaning that one or more of the leaflets 92, 94, 96 may be out of alignment with the other leaflets, causing the valve to not fully close. In such cases, conventional procedures may require the valve, which may otherwise be healthy and functional, to be replaced. Embodiments of the present invention, however, provide devices that can be installed on the aortic root 85 to support the aortic root and move the leaflets of the aortic valve back into alignment to effect more efficient coapting of the leaflets 92, 94, 96. In this way, a repair of the aortic valve may be accomplished that provides improved results as compared to conventional repairs and lasts longer than conventional repairs. Moreover, embodiments of the device described below are configured such that the device may be fitted to the existing aortic valve anatomy, thereby allowing the existing valve structure to function as well as possible, rather than attempting to make the existing valve function like a normal valve, which is more difficult, if not impossible.

Referring now to FIG. 4, a device 100 is provided that is configured to support the annulus of a valve, such as the annulus 98 of the aortic valve 65 shown in FIG. 3. The device 100 may comprise a plurality of spaced apart support members 105 that are configured to be sutured to tissue surrounding a valve opening so as to support leaflets of the valve to promote sufficient closure of the leaflets. In the embodiment depicted in FIG. 4, for example, three support members 105 are provided, corresponding to the three leaflets 92, 94, 96 of the aortic valve 65 shown in FIG. 3. Thus, in this example, each support member 105 may be configured to be sutured to the aortic annulus 98 proximate the valve opening and disposed so as to support each corresponding leaflet 92, 94, 96. In other embodiments, however, two support members 105 may be provided (e.g., in the case of a bicuspid aortic valve), or more than three support members may be used to provide a device shape that corresponds more closely to the shape of the valve opening.

In some embodiments, the device 100 may further include a connecting member 110 extending between and connecting the support members 105. One or more adjustors 115 may also be provided that are configured to engage with the connecting member 110 and to modify a length of the connecting member between two adjacent support members.

The general configuration of the device (e.g., the shape and dimensions of the support members 105, the number of support members, and/or the shape and dimensions of the connecting member 110) may be based, in some cases, on cardiac echocardiography data analysis of different pathologies. As an example, for a device 100 configured to be installed on the aortic valve, the pathologies considered may be tricuspid and bicuspid pathologies. As another example, for a device 100 configured to be installed on the mitral valve, the pathologies considered may be Barlow's disease and ischemic mitral regurgitation.

As described in greater detail below, embodiments of the device 100 are configured to adjust (e.g., increase or decrease) a dimension d of the area A circumscribed by the support members 105. For example, by modifying the length of the connecting member 110 via the adjustor 115, the dimension d may be increased to allow the device 100 to accommodate a valve with a larger valve opening or decreased to accommodate a valve with a smaller valve opening. In this way, a surgeon may be able to fit the device to the patient's anatomy in a way that will support the native structure and allow the valve to function in the most effective way possible, given the state of the valve. Although the surgeon may have an idea of the size and configuration of the patient's valve structure prior to surgery (e.g., through ultrasound and other visualization techniques, the adjustability of the connecting member 110 allows the surgeon to adjust the size of the device 100 in real time to conform to the actual size of the valve opening. Moreover, once the device 100 is installed (e.g., sutured) at the valve site, the connecting member 110 may be further adjusted via manipulation of the adjustor 115 to apply more support (e.g., through shortening of the connecting member 110) or less support (e.g., through lengthening of the connecting member 110) to the leaflets to produce the best possible closure of the valve leaflets.

In some embodiments, the connecting member 110 may be a single nitinol flat wire, or a wire made of another material, such as metal, suitable for use in the human body, that extends through each of the support members 105. For example, each support member 105 may comprise a channel 120 that extends the length of the respective support member, as shown in FIG. 5. In one embodiment, the connecting member 110 may be continuous.

In other embodiments, however, the connecting member 110 may comprise a plurality of connecting members. For example, each connecting member 110 may correspond to a different support member 105, and the at least one adjustor 115 may be configured to receive ends of two connecting members that correspond to two adjacent support members. With reference to FIG. 6, for instance, the adjustor 115 in some embodiments may be configured to receive an end 111 of one connecting member 110 from one support member through a first through opening 116 and an end 112 of another connecting member 110 from another, adjacent support member through a second through opening 117. As shown in FIG. 7, each through opening 116, 117 may include one or more engaging members 125, such as protrusions or teeth, that are configured to engage corresponding notches 128 formed or otherwise defined in the end 111, 112 of the connecting member 110.

The engaging member 125 and the end 111, 112 may be configured such that the connecting member 110 may be pushed further into the through opening 116, 117 in one direction, but a force applied in the opposite direction (e.g., pulling the connecting member out) causes the engaging member to lock the connecting member in place via the notch, thereby preventing the engaging member from being withdrawn from the through opening. In this way, a surgeon may be able to cinch the device (e.g., decrease the dimension d shown in FIG. 4). In still other cases, a mechanism may be provided to allow the connecting member 110 to be withdrawn from the adjustor 115, such as via a tool (not shown) that can be inserted into the through opening 116, 117 to move the engaging member 125 out of engagement with the notch 128, thereby allowing the connecting member to be withdrawn (e.g., to increase the dimension d shown in FIG. 4).

In still other embodiments, such as the embodiment shown in FIGS. 8A-8C, the at least one adjustor 115 may comprise an actuation portion 140. The actuation portion 140 may be configured such that actuation of the actuation portion in a first direction R1 (see FIG. 8C) draws one of the two adjacent support members towards the adjustor 115, and actuation of the actuation portion in a second direction R2 draws the other of the two adjacent support members towards the adjustor. For example, as depicted, the actuation portion 140 may include a handle 142 and a cylindrical portion 144. The cylindrical portion 144 may be attached to at least one gear 146 (shown in FIGS. 8B and 8C), and the gear 146 may be configured to engage corresponding grooves 148 defined by the ends 111, 112 of the connecting members 110. For example, the grooves 148 on each end 111, 112 of the connecting members 110 may be configured (e.g., sized and shaped) such that actuation of the actuation portion 140 in the first direction R1 engages only one of the ends 111 (not the other end 112), and actuation of the actuation portion 140 in the second direction R2 engages only the other end 112. In other cases, the actuation portion 140 may be configured such that actuation of the actuation portion in the first direction R1 draws both of the two adjacent support members towards the adjustor 115, and actuation of the actuation portion in the second direction R2 moves the two adjacent support members away from the adjustor, such as by virtue of the configuration of the grooves 148 on each end 111, 112 of the connecting members 110.

Accordingly, in some of the embodiments, the distance between adjacent support members 105 may be independently adjustable. Said differently, the surgeon may be able to increase or decrease the distance between two of the support members 105 without directly affecting the distance between the other support members, such as by actuating the adjustor 115 disposed between the two support members the distance of which the surgeon wishes to adjust. In this way, the surgeon may be able to fit embodiments of the device 100 to valve openings that may not be symmetrical, such as in valves in which one or two, but not all, of the leaflets are not functioning as normal valve leaflets for one reason or another.

In still other embodiments, the actuation portion 140 may comprise two actuation portions 140a, 140b. In such cases, each actuation portion 140a, 140b may be configured to adjust a position of the respective one of the two adjacent support members with respect to the adjustor 115. For instance, turning to FIG. 9, an actuation portion 140a, 140b may be provided at each end 111, 112 of the connecting member. The actuation portion 140a, 140b may, for example, be defined by the respective end 111, 112, such as when the end is knurled, enlarged, or otherwise configured to allow for the surgeon to easily grip and manipulate the end. In other cases, the actuation portion 140a, 140b may comprise a handle or other attachment to the respective end 111, 112.

In the depicted embodiment of FIG. 9, actuation of the respective actuation portion 140a, 140b (e.g., pulling the actuation portion in a direction S1 away from the adjustor 115) may result in the distance between the adjustor 115 and the corresponding support member decreasing. In some cases, however, as shown, the respective ends 111, 112 of the connecting members 110 may define locking extensions 150, such as spurs or other locking features, that engage corresponding features 155 of the adjustor 115 to prevent movement of the respective connecting member in a direction S2 towards the adjustor 115, effectively locking the connecting member in place. In some embodiments, a tool (not shown) may be provided that allows the locking extensions 150 to be moved out of engagement with the features 155, thereby at least temporarily allowing movement of the actuation portions 140a, 140b in the direction S2 towards the adjustor 115 to increase the distance between the adjustor and the corresponding support member.

Turning now to FIG. 10, in some embodiments, each support member 105 may comprise at least two channels, such as three channels 160a, 160b, 160c (collectively, channels 160) as depicted, extending through at least a portion of a length of the respective support member at different heights h1, h2, h3 with respect to an overall thickness t of the respective support member. In the depicted embodiment, for example, three channels 160 are provided, although in other embodiments 2, 4, or more channels may be provided as desired, provided that the thickness t of the support member 105 is able to accommodate the desired number of channels.

Each channel 160 may be configured (e.g., sized and shaped) to receive a portion of the connecting member 110 therethrough. In some embodiments, each support member 105 may further comprise a passageway 165 that is configured to allow selection of one of the channels 160 for receipt of the connecting member 110, as shown in FIGS. 11A, 11B, and 11C. Said differently, the passageway 165 may provide access between the various channels 160, such that a connecting member 110 may be moved from one channel to the next, as described below.

With reference to FIGS. 11A and 11B, for example, the passageway 165 of each support member 105 may have a first width $w_p$ that is less than a width of each respective channel we (shown in FIG. 11A) and less than a corresponding width of the connecting member received by the respective support member 105. Each support member 105, however, may be configured such that a force F applied along the thickness t of the support member serves to increase the width of the passageway from the first width $w_p$ (shown in FIG. 11A) to a second width $w_p$ (shown in FIG. 11B) so as to allow the respective connecting member 105 to pass therethrough.

In some embodiments, for example, the support member 105 may be made of a material that temporarily deforms in a proportional manner under an applied load, such as a polymer material. In this regard, application of the force F may serve to elongate the support member in a direction perpendicular to the direction of the applied force, such that the width $w_p$ of the passageway 165 increases and approaches the width we of the channels (which may also increase, although to a lesser extent than the passageway, under the applied force). As a result, the surgeon may, while applying the force F, move the connecting member 110 from one channel 160 to another via the passageway 165. For example, the connecting member 110 may be moved from the "lowest" channel 160c to the next lowest channel 160b and, if necessary, to the highest channel 160a. In this way, the device 100 shown in FIG. 4 may be configured to be adjusted in at least two dimensions (e.g., adjusting the size of the area A circumscribed by the device and adjusting the height of the support members 105) to support the valve leaflets and promote sufficient closure of the leaflets.

In FIG. 11C, for example, the connecting member 110 for one of the support members 105 is shown, in which the connecting member is positioned in the middle channel 160b. In the depicted embodiment, handles 170 are provided at either end of the support member 105 to enable a surgeon to manipulate the support member 105 so as to move the support member with respect to the connecting member 110 via the channels 160 and passageway 165 while applying force F, as described above.

The support member 105 may be configured such that the width of the passageway $w_p$ returns to the first width (shown in 11A) after the force F applied to the support member is removed. In this way, once the surgeon has achieved the desired height of the connecting member 110, the surgeon may release the support member 105, and the connecting member may be prevented from moving to other channels 160 as a result of the narrowing of the passageway 165 to its initial width $w_p$. Moreover, the height of the connecting member 110 may, in some embodiments, be independently adjustable with respect to each support member 105. As such, each support member 105 may be moved up or down relative to the connecting member 110 passing therethrough to raise or lower the portion of the valve annulus sutured to the support member as needed to obtain the proper supported configuration of the valve annulus and leaflets.

Other mechanisms may be provided for adjusting the height of portions of the device 100 with respect to other portions of the device, in addition to or instead of the channels 160 and passageway 165 depicted in FIGS. 10-11B. For example, in some embodiments, the adjustor 115 shown in FIG. 4 may comprise an adjustable hinge that is configured to adjust an angle of one portion of the connecting member 110 with respect to another portion of the connecting member 110 on either side of the adjustor. Moreover, although FIG. 5 and the examples above describe embodiments in which a connecting member extends through the entire length l of a support member 105, in some cases (e.g., in which a channel is not provided through the entire length of the support member), an end of one connecting member 110 may be received by one end of the support member (e.g., connecting that end to one adjustor 115), and an end of another connecting member may be received by the other end of the support member (e.g., connecting the other end to another adjustor 115).

Turning again to FIG. 4, in some embodiments the support members 105 may be sized to have the same length l, whereas in other embodiments the support members 105 may have different lengths, depending on application. For example, one support member 105 may, in some cases, have a longer length l than one or more of the other support members. Similarly, the lengths of the connecting member 110 between adjacent support members 105 may be independently adjusted to provide different distances between the support members, as needed. In this way, the device 100 may be custom sized to support the natural anatomy of the valve. In addition, although three support members 105 are shown in FIG. 4, in other embodiments a greater or fewer number of support members may be used. For example, in the case of a bicuspid aortic valve, two support members 105 may be used, and one of the support members may be longer than the other. Alternatively, for a bicuspid valve, two of the support members 105 may have equal lengths, and the third support member may be longer or shorter, such that the support members form a rounded isosceles triangle. In addition, in some cases, the support members 105 may be configured to have adjustable lengths l. For example, the support members 105 may be configured to allow a surgeon to trim the length l to a desired length based on a measurement of the actual size of the aortic ring to be supported.

In some embodiments, the support members 105 may have a length l that is in the range of approximately 1 cm to approximately 10 cm, so as to accommodate patients with different anatomies (e.g., small pediatric patients to large-framed, adult patients). The support members 105 and connecting member 110 may be sized together to provide support covering an area A circumscribed by the support members 105 that is equal to approximately 19 cm$^2$ (e.g., for pediatric patients) to approximately 30 cm$^2$ (e.g., for adult patients).

Turning to FIG. 10, the total thickness t of each support member 105 may be in the range of approximately 4 mm to approximately 10 mm, with the channels 160a, 160b, 160c arranged at heights h1, h2, and h3 of approximately 1 mm, 2 mm, and 3 mm, respectively, to approximately 7 mm, 8 mm, and 9 mm, respectively. In this regard, the distances between adjacent channels 160a, 160b, 160c may be approximately 1 mm to approximately 3 mm, depending on the condition of the valve and the amount of height adjustability required to support the different leaflets and areas of the valve (e.g., how much "lift" a support member 105 should be able to provide with respect to the height of other support members).

As described above, embodiments of the device 100 (e.g., shown in FIG. 4) are configured to support a valve annulus, such as the aortic valve annulus, by allowing for at least two degrees of adjustability, including adjustability of the size of the area A covered by the device (e.g., by adjusting the lengths of the support members 105 and/or the lengths of the connecting member 110 between the valves), as well as providing a mechanism to adjust the height of one or more of the support members with respect to the corresponding connecting member. Thus, embodiments of the device 100 may be used to support the annulus during a procedure operating on the aortic root or the ascending aorta, or any procedure used to treat connective tissue disorders. The annulus may be supported prophylactically, such that a percutaneous valve (for example) may be installed during a subsequent procedure if necessary. In addition, support of the annulus as described above may prevent or at least minimize the risk of future dissection or aneurysm formation, as well as the unwanted progression of diseases and failure of the native valve. In this regard, use of the device 100 may be particularly helpful for addressing conditions in patients suffering from Marfan syndrome, for example.

With reference now to FIG. 12, embodiments of a method for installing a device 100 for supporting a valve annulus are provided. According to embodiments of the method, each of a plurality of support members may be sutured to tissue surrounding a valve opening so as to support leaflets of the valve. Block 200. For example, sutures may be passed through the support members from an inner part of the shape circumscribed by the device and through the valve annulus to secure the support members to the annulus. For example, the sutures in one embodiment may be applied to three places along a support member to secure the support member to an aortic valve annulus.

As described above, a connecting member may extend between and connect the support members. A first dimension corresponding to a distance between adjacent support members may be adjusted via at least one adjustor engaged with the connecting member at block 210, and a second dimension corresponding to a height of at least one of the support members with respect to the connecting member may be adjusted at block 220. As described above, each support member may comprise at least two channels extending through at least a portion of a length of the respective support member at different heights with respect to an overall thickness of the respective support member. Each channel, in turn, may be configured to receive a portion of the connecting member therethrough, and each support member may further comprise a passageway between the at least two channels that is configured to allow selection of one of the channels for receipt of the connecting member to support the valve leaflets and promote sufficient closure of the leaflets.

As described above, adjusting the first dimension may comprise actuating an actuation portion of the at least one adjustor in a first direction to draw one of the two adjacent support members towards the adjustor. Adjusting the first dimension may comprise actuating an actuation portion of the at least one adjustor in a second direction to draw the other of the two adjacent support members towards the adjustor. In some cases, adjusting the first dimension may comprise actuating an actuation portion of the at least one adjustor in a first direction to draw the two adjacent support members towards the adjustor and actuating the actuation portion in a second direction to move the two adjacent support members away from the adjustor. Adjusting the second dimension may comprise applying a force along the thickness of the support member so as to increase a width of the passageway from a first width, that is less than a width of each respective channel and less than a corresponding width of the connecting member received by the respective support member, to a second width so as to allow the respective support member to pass therethrough, wherein the support member is configured such that the width of the passageway returns to the first width after the force applied to the support member is removed.

In still other embodiments, a length of the at least one of the plurality of support members may be adjusted at block 230. Such adjustments (e.g., to the size of the area circumscribed by the device and/or the relative height of one or more support members) may be made prior to installation and/or after the device has been sutured to the annulus. For example, the device may be adjusted after the patient has been taken off bypass, such as while the heart is beating and the surgeon has observed the real time reaction and function of the device in a working scenario.

The devices and methods depicted in the figures and described above represent only certain configurations of the device and method for supporting a valve annulus. The particular configurations and methods will depend on the patient's anatomy, the condition and location of the target site, the preferences of the practitioner, and other considerations.

Accordingly, embodiments of the device described herein and illustrated in the figures provide mechanisms for supporting a valve annulus by fitting the device to the actual pathology of the valve, rather than attempting to replicate a healthy valve (which the patient does not have). In so doing, the device allows the patient's actual valve to work as well as possible, given the valve's diseased condition.

The actual pathology of the valve is accommodated by providing for multiple dimensions of adjustability of the device, including adjustability of the size (e.g., diameter or circumscribed area) of the device as well as adjustability of the elevation or inclination of one portion of the device (e.g., one of the support members) with respect to another portion of the device. By lifting up one of the leaflets to more efficiently coapt with the other leaflet, the need to modify chordae may be reduced or eliminated. In other words, adjustments may be made at the level of the valve. Moreover, embodiments of the device allow for real time adjustments to be made, such that the surgeon is not limited to fitting the device to the patient's valve at the time of the procedure installing the device, but can also monitor the functioning of the device and any changes to the anatomy of the heart after the device is installed and can make adjustments post-operatively in a minimally invasive manner to ensure the best fit of the device to the valve and the best operation of the patient's existing valve structure.

The figures referenced above have been simplified for clarity of explanation and, thus, may not depict all of the components of the device that may be present in practice. For example, sutures attaching the device to a valve annulus and/or any predefined holes that may be included in the supporting members may not be represented in the figures. In addition, although certain mechanisms for making adjustments to the size and height of portions of the device are illustrated and described above, other mechanisms not illustrated may be used to provide the same or similar adjustment modes.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Although specific terms are employed herein, they are used in a generic and descriptive sense only and not for purposes of limitation.

What is claimed is:

1. A device for supporting a valve annulus comprising:
   a plurality of spaced apart support members configured to be sutured to tissue surrounding a valve opening so as to support leaflets of the valve to promote sufficient closure of the leaflets;
   a connecting member extending between and connecting the support members; and
   at least one adjustor engaged with connecting a member and configured to modify a length of the connecting member between two adjacent support members,
   wherein the at least one adjustor comprises an actuation portion and the device is configured to be adjusted in at least two dimensions to support the valve leaflets and promote sufficient closure of the leaflets,
   wherein actuation of the actuation portion in a first direction draws one of the two adjacent support members towards the adjustor, and
   wherein actuation of the actuation portion in a second direction draws the other of the two adjacent support members towards the adjustor.

2. The device of claim 1, wherein the device comprises at least three support members.

3. The device of claim 1, wherein the connecting member comprises a plurality of connecting members.

4. The device of claim 3, wherein each connecting member corresponds to a different support member, wherein the at least one adjustor is configured to receive ends of two connecting members corresponding to two adjacent support members.

5. The device of claim 1, wherein the actuation portion comprises two actuation portions, each actuation portion configured to adjust a position of a respective one of the two adjacent support members with respect to the adjustor.

6. The device of claim 1, wherein the at least one adjustor comprises an adjustable hinge that is configured to adjust an angle of one portion of the connecting member with respect to another portion of the connecting member on either side of the adjustor.

7. The device of claim 1, wherein the distance between adjacent support members is independently adjustable.

8. The device of claim 1, wherein the connecting member comprises nitinol.

9. The device of claim 1, wherein each support member comprises:
   at least two channels configured to receive a portion of the connecting member and each channel extends through at least a portion of a length of the respective support member at different heights with respect to an overall thickness of the respective support member; and
   a passageway between the at least two channels,
   wherein each passageway is configured to allow selection of one of the channels for receipt of the connecting member,
   wherein the passageway of each support member has a first width that is less than a width of each respective channel and less than a corresponding width of the connecting member received by the respective support member, and
   wherein each support member is configured such that a force applied along the thickness of the support member serves to increase a width of the passageway from the first width to a second width so as to allow the respective connecting member to pass therethrough.

10. The device of claim 9, wherein the support member is configured such that the width of the passageway returns to the first width after the force applied to the support member is removed.

11. The device of claim 1, wherein each support member comprises at least three channels.

12. The device of claim 1, wherein each support member defines a length, and wherein at least two of the support members have different lengths.

13. The device of claim 1, wherein each support member defines a length, and wherein the length of the support members is adjustable.

14. A method for supporting a valve annulus comprising:
   suturing each of a plurality of support members to tissue surrounding a valve opening so as to support leaflets of the valve, wherein a connecting member extends between and connects the support members;
   adjusting a first dimension corresponding to a distance between adjacent support members via at least one adjustor engaged with the connecting member; and
   adjusting a second dimension corresponding to a height of at least one of the support members with respect to the connecting member,
   wherein adjusting the first dimension comprises actuating an actuation portion of the at least one adjustor
   wherein actuating the actuation portion of the at least one adjustor in a first direction draws one of the two adjacent support members towards the adjustor; and
   wherein actuating the actuation portion of the at least one adjustor in a second direction draws the other of the two adjacent support members toward the adjustor.

15. The method of claim 14, wherein actuating the actuation portion of the at least one adjustor in a first direction draws the two adjacent support members towards the adjustor and actuating the actuation portion in a second direction moves the two adjacent support members away from the adjustor.

16. The method of claim 14, wherein adjusting the second dimension comprises adjusting an adjustable hinge that is configured to adjust an angle of one portion of the connecting member with respect to another portion of the connecting member on either side of the adjustor.

17. The method of claim 14 further comprising adjusting a length of at least one of the plurality of support members.

* * * * *